United States Patent
Randall et al.

(10) Patent No.: US 7,935,141 B2
(45) Date of Patent: May 3, 2011

(54) VARIABLE SPEED STENT DELIVERY SYSTEM

(75) Inventors: Michael Randall, Mission Viejo, CA (US); John Fulkerson, Rancho Santa Margarita, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1238 days.

(21) Appl. No.: 11/505,185

(22) Filed: Aug. 16, 2006

(65) Prior Publication Data
US 2007/0060999 A1 Mar. 15, 2007

Related U.S. Application Data

(60) Provisional application No. 60/709,314, filed on Aug. 17, 2005.

(51) Int. Cl.
*A61F 2/06* (2006.01)
(52) U.S. Cl. .................................. 623/1.11; 606/108
(58) Field of Classification Search ................. 623/1.11, 623/1.12, 1.23; 606/108
See application file for complete search history.

(56) References Cited

U.S. PATENT DOCUMENTS

| | | | | |
|---|---|---|---|---|
| 1,988,060 A | * | 1/1935 | Vollenbroich | 57/62 |
| 2,934,211 A | * | 4/1960 | Shivek | 211/59.3 |
| 2,939,680 A | * | 6/1960 | Powell | 254/340 |
| 3,070,057 A | * | 12/1962 | Dezzani | 226/128 |
| 3,562,427 A | * | 2/1971 | Yano et al. | 360/70 |
| 3,585,707 A | | 6/1971 | Stevens | |
| 3,871,382 A | | 3/1975 | Mann | |
| 3,881,423 A | * | 5/1975 | Woods et al. | 104/25 |
| 4,256,113 A | | 3/1981 | Chamness | |
| 4,553,545 A | | 11/1985 | Maass et al. | |
| 4,580,568 A | | 4/1986 | Gianturco | |
| 4,616,648 A | * | 10/1986 | Simpson | 606/108 |
| 4,649,922 A | | 3/1987 | Wiktor | |
| 4,665,918 A | | 5/1987 | Garza et al. | |

(Continued)

FOREIGN PATENT DOCUMENTS
CA 2155527 A1 8/1994
(Continued)

OTHER PUBLICATIONS

Nov. 30, 2007 International Search Report in international application No. PCT/EP2007/058205 filed on Aug. 7, 2007.

(Continued)

*Primary Examiner* — Todd E Manahan
*Assistant Examiner* — Erin Colello
(74) *Attorney, Agent, or Firm* — Rutan & Tucker, LLP (57) ABSTRACT

A delivery system for deploying a medical device, such as a stent, at increasing deployment speed is described. The system comprises a catheter comprising a catheter shaft, a retractable sheath slidably mounted on the catheter shaft, and the device in a compressed state sandwiched between the shaft and sheath. A control handle is included with a housing and knobs for a user to apply a rotary or other force to retract the sheath. The sheath is attached to a slider that is mounted on a slide rod and attached to a drive belt. A take up pulley is provided in the housing and connected to the belt input knob, so that the pulley turns when the knob is turned. The belt is attached to the pulley so that the drive is wound onto the rotating pulley. As the belt winds upon the pulley, the overall outside diameter of the pulley increases, thereby increasing the deployment speed.

5 Claims, 3 Drawing Sheets

U.S. PATENT DOCUMENTS

| | | | |
|---|---|---|---|
| 4,723,547 A | 2/1988 | Kullas et al. | |
| 4,733,665 A | 3/1988 | Palmaz | |
| 4,739,762 A | 4/1988 | Palmaz | |
| 4,760,622 A * | 8/1988 | Rohrman | 16/196 |
| 4,771,773 A | 9/1988 | Kropf | |
| 4,800,882 A | 1/1989 | Gianturco | |
| 4,856,516 A | 8/1989 | Hillstead | |
| 4,886,062 A | 12/1989 | Wiktor | |
| 4,889,112 A | 12/1989 | Schachner et al. | |
| 4,913,141 A | 4/1990 | Hillstead | |
| 4,913,683 A | 4/1990 | Gregory | |
| 4,969,458 A | 11/1990 | Wiktor | |
| 4,990,151 A | 2/1991 | Wallsten | |
| 5,019,090 A | 5/1991 | Pinchuk | |
| 5,026,377 A | 6/1991 | Burton et al. | |
| 5,045,072 A | 9/1991 | Castillo et al. | |
| 5,049,128 A | 9/1991 | Duquette | |
| 5,054,162 A * | 10/1991 | Rogers | 16/198 |
| 5,102,417 A | 4/1992 | Palmaz | |
| 5,104,404 A | 4/1992 | Wolff | |
| 5,116,365 A | 5/1992 | Hillstead | |
| 5,133,732 A | 7/1992 | Wiktor | |
| 5,135,536 A | 8/1992 | Hillstead | |
| 5,161,547 A | 11/1992 | Tower | |
| 5,163,941 A | 11/1992 | Garth et al. | |
| 5,190,552 A | 3/1993 | Kelman | |
| 5,201,757 A | 4/1993 | Heyn et al. | |
| 5,203,774 A | 4/1993 | Gilson et al. | |
| 5,209,754 A | 5/1993 | Ahluwalia | |
| 5,224,939 A | 7/1993 | Holman et al. | |
| 5,228,452 A | 7/1993 | Samson | |
| 5,242,423 A | 9/1993 | Goodsir et al. | |
| 5,254,107 A | 10/1993 | Soltesz | |
| 5,275,622 A | 1/1994 | Lazarus et al. | |
| 5,279,596 A | 1/1994 | Castaneda et al. | |
| 5,282,824 A | 2/1994 | Gianturco | |
| 5,290,295 A | 3/1994 | Querals et al. | |
| 5,290,310 A | 3/1994 | Makower et al. | |
| 5,292,331 A | 3/1994 | Boneau | |
| 5,312,351 A | 5/1994 | Gerrone | |
| 5,312,363 A | 5/1994 | Ryan et al. | |
| 5,334,147 A | 8/1994 | Johnson | |
| 5,336,192 A | 8/1994 | Palestrant | |
| 5,346,498 A | 9/1994 | Greelis et al. | |
| 5,380,283 A | 1/1995 | Johnson | |
| 5,383,892 A | 1/1995 | Cardon et al. | |
| 5,387,235 A | 2/1995 | Chuter | |
| 5,391,172 A | 2/1995 | Williams et al. | |
| 5,411,507 A | 5/1995 | Heckele | |
| 5,415,664 A | 5/1995 | Pinchuk | |
| 5,417,708 A | 5/1995 | Hall et al. | |
| 5,421,955 A | 6/1995 | Lau et al. | |
| 5,433,723 A | 7/1995 | Lindenberg et al. | |
| 5,443,477 A | 8/1995 | Marin et al. | |
| 5,449,373 A | 9/1995 | Pinchasik et al. | |
| 5,456,694 A | 10/1995 | Marin et al. | |
| 5,456,713 A | 10/1995 | Chuter | |
| 5,458,615 A | 10/1995 | Klemm et al. | |
| 5,466,221 A | 11/1995 | Zadini et al. | |
| 5,480,423 A | 1/1996 | Ravenscroft et al. | |
| 5,507,768 A | 4/1996 | Lau et al. | |
| 5,507,769 A | 4/1996 | Marin et al. | |
| 5,509,900 A | 4/1996 | Kirkman | |
| 5,514,154 A | 5/1996 | Lau et al. | |
| 5,531,690 A | 7/1996 | Solar | |
| 5,536,248 A | 7/1996 | Weaver et al. | |
| 5,538,510 A | 7/1996 | Fontirroche et al. | |
| 5,556,389 A | 9/1996 | Liprie | |
| 5,562,726 A | 10/1996 | Chuter | |
| 5,562,728 A | 10/1996 | Lazarus et al. | |
| 5,569,296 A | 10/1996 | Marin et al. | |
| 5,571,086 A | 11/1996 | Kaplan et al. | |
| 5,571,172 A | 11/1996 | Chin | |
| 5,573,530 A | 11/1996 | Fleury et al. | |
| 5,578,074 A | 11/1996 | Mirigian | |
| 5,591,172 A | 1/1997 | Bachmann et al. | |
| 5,591,196 A | 1/1997 | Marin et al. | |
| 5,601,568 A | 2/1997 | Chevillon et al. | |
| 5,603,721 A | 2/1997 | Lau et al. | |
| 5,605,530 A | 2/1997 | Fischell et al. | |
| 5,609,627 A | 3/1997 | Goicoechea et al. | |
| 5,618,300 A | 4/1997 | Marin et al. | |
| 5,628,755 A | 5/1997 | Heller et al. | |
| 5,630,801 A | 5/1997 | Roussigne et al. | |
| 5,645,076 A | 7/1997 | Yoon | |
| 5,649,906 A | 7/1997 | Gory et al. | |
| 5,666,970 A | 9/1997 | Smith | |
| 5,669,936 A | 9/1997 | Lazarus | |
| 5,672,179 A | 9/1997 | Garth et al. | |
| 5,674,278 A | 10/1997 | Boneau | |
| 5,681,322 A | 10/1997 | Hartigan, Jr. | |
| 5,683,345 A | 11/1997 | Waksman et al. | |
| 5,683,451 A | 11/1997 | Lenker et al. | |
| 5,690,644 A | 11/1997 | Yurek et al. | |
| 5,693,084 A | 12/1997 | Chuter | |
| 5,695,498 A | 12/1997 | Tower | |
| 5,695,499 A | 12/1997 | Helgerson et al. | |
| 5,695,517 A | 12/1997 | Marin et al. | |
| 5,697,936 A | 12/1997 | Shipko et al. | |
| 5,697,949 A | 12/1997 | Giurtino et al. | |
| 5,704,914 A | 1/1998 | Stocking et al. | |
| 5,707,376 A * | 1/1998 | Kavteladze et al. | 623/1.11 |
| 5,709,703 A | 1/1998 | Lukic et al. | |
| 5,713,917 A | 2/1998 | Leonhardt et al. | |
| 5,713,948 A | 2/1998 | Uflacker | |
| 5,716,365 A | 2/1998 | Goicoechea et al. | |
| 5,716,393 A | 2/1998 | Lindenberg et al. | |
| 5,720,776 A | 2/1998 | Chuter et al. | |
| 5,725,534 A | 3/1998 | Rasmussen | |
| 5,728,158 A | 3/1998 | Lau et al. | |
| 5,733,303 A | 3/1998 | Israel et al. | |
| 5,735,893 A | 4/1998 | Lau et al. | |
| 5,738,667 A | 4/1998 | Solar | |
| 5,741,298 A | 4/1998 | MacLeod | |
| 5,749,921 A | 5/1998 | Lenker et al. | |
| 5,755,777 A | 5/1998 | Chuter | |
| 5,759,186 A | 6/1998 | Bachmann et al. | |
| 5,766,184 A | 6/1998 | Matsuno et al. | |
| 5,769,871 A | 6/1998 | Mers Kelly et al. | |
| 5,776,141 A | 7/1998 | Klein et al. | |
| 5,776,142 A | 7/1998 | Gunderson | |
| 5,776,161 A | 7/1998 | Globerman et al. | |
| 5,776,186 A | 7/1998 | Uflacker | |
| 5,780,807 A | 7/1998 | Saunders | |
| 5,782,855 A | 7/1998 | Lau et al. | |
| 5,788,707 A | 8/1998 | Del Toro et al. | |
| 5,795,325 A | 8/1998 | Valley et al. | |
| 5,800,456 A | 9/1998 | Maeda et al. | |
| 5,800,520 A | 9/1998 | Fogarty et al. | |
| 5,807,327 A | 9/1998 | Green et al. | |
| 5,810,768 A | 9/1998 | Lopez | |
| 5,810,837 A | 9/1998 | Hofmann et al. | |
| 5,810,869 A | 9/1998 | Kaplan et al. | |
| 5,810,872 A | 9/1998 | Kanesaka et al. | |
| 5,814,062 A | 9/1998 | Sepetka et al. | |
| 5,824,058 A | 10/1998 | Ravenscroft et al. | |
| 5,833,694 A * | 11/1998 | Poncet | 623/1.11 |
| 5,840,064 A | 11/1998 | Liprie | |
| 5,843,088 A | 12/1998 | Barra et al. | |
| 5,843,092 A | 12/1998 | Heller et al. | |
| 5,843,120 A | 12/1998 | Israel et al. | |
| 5,843,244 A | 12/1998 | Pelton et al. | |
| 5,851,210 A | 12/1998 | Torossian | |
| 5,860,998 A | 1/1999 | Robinson et al. | |
| RE36,104 E | 2/1999 | Solar | |
| 5,868,755 A | 2/1999 | Kanner et al. | |
| 5,873,906 A | 2/1999 | Lau et al. | |
| 5,879,382 A | 3/1999 | Boneau | |
| 5,891,154 A | 4/1999 | Loeffler | |
| 5,906,579 A | 5/1999 | Vander Salm et al. | |
| 5,906,619 A | 5/1999 | Olson et al. | |
| 5,913,897 A | 6/1999 | Corso, Jr. et al. | |
| 5,919,225 A | 7/1999 | Lau et al. | |
| 5,925,061 A | 7/1999 | Ogi et al. | |
| 5,928,246 A | 7/1999 | Gordon et al. | |
| 5,931,842 A | 8/1999 | Goldsteen et al. | |
| 5,944,727 A | 8/1999 | Ahari et al. | |

| Patent No. | Date | Inventor(s) | Ref |
|---|---|---|---|
| 5,951,585 A | 9/1999 | Cathcart et al. | |
| 5,961,536 A | 10/1999 | Mickley et al. | |
| 5,968,052 A * | 10/1999 | Sullivan et al. | 623/1.11 |
| 5,968,053 A | 10/1999 | Revelas | |
| 5,968,068 A | 10/1999 | Dehdashtian et al. | |
| 5,968,069 A | 10/1999 | Dusbabek et al. | |
| 5,972,018 A | 10/1999 | Israel et al. | |
| 5,980,515 A | 11/1999 | Tu | |
| 5,984,225 A | 11/1999 | Enzinna | |
| 5,992,000 A | 11/1999 | Humphrey et al. | |
| 5,997,562 A | 12/1999 | Zadno-Azizi et al. | |
| 6,004,328 A | 12/1999 | Solar | |
| 6,015,429 A | 1/2000 | Lau et al. | |
| 6,019,778 A | 2/2000 | Wilson et al. | |
| 6,027,509 A | 2/2000 | Schatz et al. | |
| 6,039,744 A | 3/2000 | Forber | |
| 6,039,749 A | 3/2000 | Marin et al. | |
| 6,042,597 A | 3/2000 | Kveen et al. | |
| 6,045,536 A | 4/2000 | Meier et al. | |
| 6,071,263 A | 6/2000 | Kirkman | |
| 6,071,286 A | 6/2000 | Mawad | |
| 6,077,295 A | 6/2000 | Limon et al. | |
| 6,080,140 A | 6/2000 | Swaminathan et al. | |
| 6,083,194 A | 7/2000 | Lopez | |
| 6,090,035 A | 7/2000 | Campbell et al. | |
| 6,090,063 A * | 7/2000 | Makower et al. | 604/13 |
| 6,090,128 A | 7/2000 | Douglas | |
| 6,096,009 A | 8/2000 | Windheuser et al. | |
| 6,096,045 A | 8/2000 | Del Toro et al. | |
| 6,096,056 A | 8/2000 | Brown | |
| 6,102,942 A | 8/2000 | Ahari | |
| 6,110,191 A | 8/2000 | Dehdashtian et al. | |
| 6,113,607 A | 9/2000 | Lau et al. | |
| 6,117,140 A | 9/2000 | Munsinger | |
| 6,117,165 A | 9/2000 | Becker | |
| 6,117,167 A | 9/2000 | Goicoechea et al. | |
| 6,123,723 A | 9/2000 | Konya et al. | |
| 6,129,755 A | 10/2000 | Mathis et al. | |
| 6,136,007 A | 10/2000 | Goldsteen et al. | |
| 6,136,572 A | 10/2000 | Benatti et al. | |
| 6,143,014 A | 11/2000 | Dehdashtian et al. | |
| 6,143,021 A | 11/2000 | Staehle | |
| 6,146,415 A | 11/2000 | Fitz | |
| 6,149,680 A | 11/2000 | Shelso et al. | |
| 6,156,053 A | 12/2000 | Gandhi et al. | |
| 6,156,054 A | 12/2000 | Zadno-Azizi et al. | |
| 6,156,063 A | 12/2000 | Douglas | |
| 6,159,228 A | 12/2000 | Frid et al. | |
| 6,159,239 A * | 12/2000 | Greenhalgh | 623/1.13 |
| 6,167,315 A | 12/2000 | Coe et al. | |
| 6,168,610 B1 | 1/2001 | Marin et al. | |
| 6,168,617 B1 | 1/2001 | Blaeser et al. | |
| 6,174,327 B1 | 1/2001 | Mertens et al. | |
| 6,183,509 B1 | 2/2001 | Dibie | |
| 6,190,360 B1 | 2/2001 | Iancea et al. | |
| 6,190,393 B1 | 2/2001 | Bevier et al. | |
| 6,190,406 B1 | 2/2001 | Duerig et al. | |
| 6,203,550 B1 | 3/2001 | Olson | |
| 6,203,558 B1 | 3/2001 | Dusbabek et al. | |
| 6,210,422 B1 | 4/2001 | Douglas | |
| 6,217,585 B1 | 4/2001 | Houser et al. | |
| 6,224,608 B1 | 5/2001 | Ciccolella et al. | |
| 6,238,402 B1 * | 5/2001 | Sullivan et al. | 606/108 |
| 6,238,415 B1 | 5/2001 | Sepetka et al. | |
| 6,241,692 B1 | 6/2001 | Tu et al. | |
| 6,245,100 B1 | 6/2001 | Davila et al. | |
| 6,248,122 B1 * | 6/2001 | Klumb et al. | 606/194 |
| 6,251,132 B1 | 6/2001 | Ravenscroft et al. | |
| 6,254,608 B1 | 7/2001 | Solar | |
| 6,264,689 B1 | 7/2001 | Colgan et al. | |
| 6,270,521 B1 | 8/2001 | Fischell et al. | |
| 6,273,895 B1 | 8/2001 | Pinchuk et al. | |
| 6,287,322 B1 | 9/2001 | Zhu et al. | |
| 6,312,407 B1 | 11/2001 | Zadno-Azizi et al. | |
| 6,319,262 B1 | 11/2001 | Bates et al. | |
| 6,332,403 B1 | 12/2001 | Weise et al. | |
| 6,342,067 B1 | 1/2002 | Mathis et al. | |
| 6,344,053 B1 | 2/2002 | Boneau | |
| 6,348,065 B1 | 2/2002 | Brown et al. | |
| 6,358,274 B1 | 3/2002 | Thompson | |
| 6,375,676 B1 | 4/2002 | Cox | |
| 6,383,211 B1 | 5/2002 | Staehle | |
| 6,391,050 B1 | 5/2002 | Broome | |
| 6,391,051 B2 | 5/2002 | Sullivan, III et al. | |
| 6,395,020 B1 | 5/2002 | Ley et al. | |
| 6,402,760 B1 * | 6/2002 | Fedida | 606/108 |
| 6,413,269 B1 | 7/2002 | Bui et al. | |
| 6,443,979 B1 | 9/2002 | Stalker et al. | |
| 6,443,982 B1 | 9/2002 | Israel et al. | |
| 6,461,381 B1 | 10/2002 | Israel et al. | |
| 6,488,703 B1 | 12/2002 | Kveen et al. | |
| 6,500,248 B1 | 12/2002 | Hayashi | |
| 6,514,261 B1 | 2/2003 | Randall et al. | |
| 6,517,569 B2 | 2/2003 | Mikus et al. | |
| 6,520,983 B1 | 2/2003 | Colgan et al. | |
| 6,527,779 B1 | 3/2003 | Rourke | |
| 6,572,643 B1 | 6/2003 | Gharibadeh | |
| 6,599,296 B1 * | 7/2003 | Gillick et al. | 606/108 |
| 6,613,014 B1 | 9/2003 | Chi | |
| 6,613,075 B1 | 9/2003 | Healy et al. | |
| 6,629,981 B2 | 10/2003 | Bui et al. | |
| 6,645,238 B2 | 11/2003 | Smith | |
| 6,652,506 B2 | 11/2003 | Bowe et al. | |
| 6,660,031 B2 | 12/2003 | Tran et al. | |
| 6,660,827 B2 | 12/2003 | Loomis et al. | |
| 6,663,666 B1 | 12/2003 | Quiachon et al. | |
| 6,695,862 B2 | 2/2004 | Cox et al. | |
| 6,716,190 B1 | 4/2004 | Glines et al. | |
| 6,716,238 B2 * | 4/2004 | Elliott | 623/1.11 |
| 6,749,627 B2 | 6/2004 | Thompson et al. | |
| 6,755,854 B2 | 6/2004 | Gillick et al. | |
| 6,773,446 B1 | 8/2004 | Dwyer et al. | |
| 6,786,918 B1 | 9/2004 | Krivoruchko et al. | |
| 6,821,292 B2 | 11/2004 | Pazienza et al. | |
| 6,866,669 B2 * | 3/2005 | Buzzard et al. | 606/108 |
| 6,884,259 B2 * | 4/2005 | Tran et al. | 623/1.12 |
| 6,911,039 B2 | 6/2005 | Shiu et al. | |
| 6,913,613 B2 * | 7/2005 | Schwarz et al. | 606/206 |
| 6,939,352 B2 * | 9/2005 | Buzzard et al. | 606/108 |
| 6,939,370 B2 | 9/2005 | Hartley et al. | |
| 7,033,368 B2 | 4/2006 | Rourke | |
| 7,052,511 B2 | 5/2006 | Weldon et al. | |
| 7,122,050 B2 | 10/2006 | Randall et al. | |
| 7,172,617 B2 | 2/2007 | Colgan et al. | |
| 7,294,135 B2 * | 11/2007 | Stephens et al. | 606/108 |
| 7,323,006 B2 * | 1/2008 | Andreas et al. | 623/1.11 |
| 7,381,216 B2 * | 6/2008 | Buzzard et al. | 623/1.11 |
| D576,725 S | 9/2008 | Shumer et al. | |
| D578,216 S | 10/2008 | Dorn et al. | |
| D578,643 S | 10/2008 | Shumer et al. | |
| D578,644 S | 10/2008 | Shumer et al. | |
| D578,645 S | 10/2008 | Shumer et al. | |
| 7,506,650 B2 * | 3/2009 | Lowe et al. | 128/830 |
| 7,550,001 B2 | 6/2009 | Dorn et al. | |
| 7,553,322 B2 | 6/2009 | Dorn et al. | |
| D598,543 S | 8/2009 | Vogel et al. | |
| 7,582,054 B2 * | 9/2009 | Okada | 600/106 |
| 2001/0007082 A1 | 7/2001 | Dusbabek et al. | |
| 2001/0044621 A1 * | 11/2001 | Klumb et al. | 606/1 |
| 2001/0051822 A1 | 12/2001 | Stack et al. | |
| 2002/0004663 A1 | 1/2002 | Gittings et al. | |
| 2002/0035394 A1 | 3/2002 | Fierens et al. | |
| 2002/0116044 A1 | 8/2002 | Cottone et al. | |
| 2002/0151955 A1 | 10/2002 | Tran et al. | |
| 2002/0183827 A1 | 12/2002 | Derus et al. | |
| 2002/0188341 A1 * | 12/2002 | Elliott | 623/1.1 |
| 2003/0028236 A1 | 2/2003 | Gillick et al. | |
| 2003/0049295 A1 | 3/2003 | Guggenbichler et al. | |
| 2003/0050686 A1 | 3/2003 | Raeder-Devens et al. | |
| 2003/0074045 A1 * | 4/2003 | Buzzard et al. | 623/1.11 |
| 2003/0163085 A1 | 8/2003 | Tanner et al. | |
| 2003/0167060 A1 * | 9/2003 | Buzzard et al. | 606/108 |
| 2003/0191516 A1 * | 10/2003 | Weldon et al. | 623/1.12 |
| 2004/0006380 A1 * | 1/2004 | Buck et al. | 623/1.11 |
| 2004/0098083 A1 * | 5/2004 | Tran et al. | 623/1.11 |
| 2004/0143160 A1 | 7/2004 | Couvillon | |
| 2004/0148009 A1 * | 7/2004 | Buzzard et al. | 623/1.12 |
| 2004/0153137 A1 | 8/2004 | Gaschino et al. | |

| Publication No. | Date | Inventor | Class |
|---|---|---|---|
| 2004/0181239 A1* | 9/2004 | Dorn et al. | 606/108 |
| 2004/0186547 A1 | 9/2004 | Dorn et al. | |
| 2004/0193180 A1* | 9/2004 | Buzzard et al. | 606/108 |
| 2004/0193283 A1 | 9/2004 | Rioux et al. | |
| 2004/0199240 A1 | 10/2004 | Dorn | |
| 2005/0004515 A1* | 1/2005 | Hart et al. | 604/95.04 |
| 2005/0021123 A1* | 1/2005 | Dorn et al. | 623/1.11 |
| 2005/0027306 A1 | 2/2005 | Krivoruchko et al. | |
| 2005/0033402 A1* | 2/2005 | Cully et al. | 623/1.11 |
| 2005/0060016 A1* | 3/2005 | Wu et al. | 623/1.11 |
| 2005/0080476 A1* | 4/2005 | Gunderson et al. | 623/1.11 |
| 2005/0085851 A1* | 4/2005 | Fiehler et al. | 606/213 |
| 2005/0090890 A1 | 4/2005 | Wu et al. | |
| 2005/0149159 A1* | 7/2005 | Andreas et al. | 623/1.11 |
| 2005/0182475 A1 | 8/2005 | Jen et al. | |
| 2005/0209670 A1 | 9/2005 | George et al. | |
| 2005/0209672 A1 | 9/2005 | George et al. | |
| 2005/0209674 A1 | 9/2005 | Kutscher et al. | |
| 2005/0240254 A1 | 10/2005 | Austin | |
| 2005/0256562 A1 | 11/2005 | Clerc et al. | |
| 2005/0273151 A1* | 12/2005 | Fulkerson et al. | 623/1.11 |
| 2005/0288764 A1* | 12/2005 | Snow et al. | 623/1.11 |
| 2006/0058866 A1* | 3/2006 | Cully et al. | 623/1.11 |
| 2006/0074477 A1 | 4/2006 | Berthiaume et al. | |
| 2006/0085057 A1 | 4/2006 | George et al. | |
| 2006/0100686 A1 | 5/2006 | Bolduc et al. | |
| 2006/0167467 A1 | 7/2006 | Rourke | |
| 2006/0259124 A1 | 11/2006 | Matsuoka et al. | |
| 2006/0276873 A1* | 12/2006 | Sato | 623/1.11 |
| 2007/0016164 A1 | 1/2007 | Dudney et al. | |
| 2007/0050006 A1 | 3/2007 | Lavelle | |
| 2007/0055339 A1 | 3/2007 | George et al. | |
| 2007/0055342 A1 | 3/2007 | Wu et al. | |
| 2007/0073379 A1 | 3/2007 | Chang | |
| 2007/0073389 A1* | 3/2007 | Bolduc et al. | 623/1.36 |
| 2007/0088421 A1 | 4/2007 | Loewen | |
| 2007/0100420 A1 | 5/2007 | Kavanagh et al. | |
| 2007/0100422 A1 | 5/2007 | Shumer et al. | |
| 2007/0100429 A1 | 5/2007 | Wu et al. | |
| 2007/0112409 A1 | 5/2007 | Wu et al. | |
| 2007/0118201 A1 | 5/2007 | Pappas et al. | |
| 2007/0118206 A1 | 5/2007 | Colgan et al. | |
| 2007/0168014 A1 | 7/2007 | Jimenez et al. | |
| 2007/0191864 A1 | 8/2007 | Shumer | |
| 2007/0191865 A1 | 8/2007 | Pappas | |
| 2007/0191925 A1* | 8/2007 | Dorn | 623/1.12 |
| 2007/0194483 A1 | 8/2007 | Guggenbichler et al. | |
| 2007/0233222 A1 | 10/2007 | Roeder et al. | |
| 2007/0244540 A1 | 10/2007 | Pryor | |
| 2007/0255390 A1 | 11/2007 | Ducke et al. | |
| 2009/0024133 A1* | 1/2009 | Keady et al. | 606/99 |
| 2009/0099638 A1* | 4/2009 | Grewe | 623/1.11 |
| 2010/0004606 A1* | 1/2010 | Hansen et al. | 604/264 |
| 2010/0036472 A1* | 2/2010 | Papp | 623/1.11 |
| 2010/0094399 A1 | 4/2010 | Dorn et al. | |
| 2010/0168756 A1 | 7/2010 | Dorn et al. | |
| 2010/0174290 A1 | 7/2010 | Wuebbeling et al. | |

FOREIGN PATENT DOCUMENTS

| | | |
|---|---|---|
| DE | 2544371 A1 | 4/1976 |
| DE | 03132323 A1 | 4/1983 |
| DE | 295 16 712 U | 12/1995 |
| DE | 04420142 A1 | 12/1995 |
| DE | 19539449 A1 | 4/1997 |
| DE | 29717110 U1 | 11/1997 |
| DE | 298 16 878 | 12/1998 |
| DE | 29522101 | 12/1999 |
| DE | 19901530 A1 | 7/2000 |
| DE | 19936059 A1 | 2/2001 |
| DE | 20000659 U1 | 5/2001 |
| DE | 69521346 T2 | 4/2002 |
| EP | 0436303 A1 | 7/1991 |
| EP | 0518838 A1 | 12/1992 |
| EP | 0564894 A1 | 10/1993 |
| EP | 0611556 A1 | 8/1994 |
| EP | 0630657 A1 | 12/1994 |
| EP | 0633756 B1 | 1/1995 |
| EP | 688545 A1 | 12/1995 |
| EP | 0699451 A2 | 3/1996 |
| EP | 712614 A1 | 5/1996 |
| EP | 0747021 A2 | 12/1996 |
| EP | 0752896 B1 | 1/1997 |
| EP | 790041 A2 | 8/1997 |
| EP | 792627 A2 | 9/1997 |
| EP | 0873733 A1 | 10/1998 |
| EP | 0876804 A1 | 11/1998 |
| EP | 0947212 A2 | 10/1999 |
| EP | 1025813 A2 | 8/2000 |
| EP | 1078611 A1 | 2/2001 |
| EP | 1095634 A2 | 5/2001 |
| EP | 1117341 A1 | 7/2001 |
| EP | 1132058 | 9/2001 |
| EP | 1155664 A2 | 11/2001 |
| EP | 1181906 A2 | 2/2002 |
| EP | 1199051 A2 | 4/2002 |
| EP | 1290989 A2 | 3/2003 |
| EP | 1299050 B1 | 4/2003 |
| EP | 1302178 A2 | 4/2003 |
| EP | 1383446 A1 | 1/2004 |
| EP | 1440671 A2 | 7/2004 |
| EP | 1447057 A1 | 8/2004 |
| EP | 1447058 A1 | 8/2004 |
| EP | 1637092 A2 | 3/2006 |
| FR | 2 760 351 | 9/1998 |
| FR | 2797761 A1 | 3/2001 |
| FR | 2797781 A1 | 3/2001 |
| WO | WO-9521593 A1 | 8/1995 |
| WO | WO-9526775 A1 | 10/1995 |
| WO | WO-9618359 A1 | 6/1996 |
| WO | WO-9820811 A1 | 5/1998 |
| WO | WO-9823241 A2 | 6/1998 |
| WO | WO 98 30173 A | 7/1998 |
| WO | WO-9852496 A1 | 11/1998 |
| WO | WO-9904728 A1 | 2/1999 |
| WO | WO-9925280 A1 | 5/1999 |
| WO | WO-9944541 A1 | 9/1999 |
| WO | WO-9947075 A1 | 9/1999 |
| WO | WO-9951167 A2 | 10/1999 |
| WO | WO 00/02503 | 1/2000 |
| WO | WO-0000104 A1 | 1/2000 |
| WO | WO-0002503 A1 | 1/2000 |
| WO | WO 0016718 A1 | 3/2000 |
| WO | WO-0018330 A1 | 4/2000 |
| WO | WO-0071059 A1 | 11/2000 |
| WO | WO-0078246 A2 | 12/2000 |
| WO | WO-0078248 A1 | 12/2000 |
| WO | WO-0132102 | 5/2001 |
| WO | WO-0134061 A1 | 5/2001 |
| WO | WO 01/47436 A2 | 7/2001 |
| WO | WO-0147436 A2 | 7/2001 |
| WO | WO-0158387 A1 | 8/2001 |
| WO | WO/01/98421 | 11/2001 |
| WO | WO-0189421 A2 | 11/2001 |
| WO | WO 02/03889 A2 | 1/2002 |
| WO | WO-0203888 A2 | 1/2002 |
| WO | WO-0203889 A2 | 1/2002 |
| WO | WO-02066094 A2 | 8/2002 |
| WO | WO-02083036 A2 | 10/2002 |
| WO | WO-02087470 A1 | 11/2002 |
| WO | WO-02102279 A2 | 12/2002 |
| WO | WO-03002020 A2 | 1/2003 |
| WO | 03061724 A2 | 7/2003 |
| WO | WO-2005004515 A1 | 1/2005 |
| WO | WO-2005039448 A1 | 5/2005 |
| WO | WO-2005053574 A2 | 6/2005 |
| WO | 2005062980 A2 | 7/2005 |
| WO | 2005065200 A2 | 7/2005 |
| WO | 2005117759 A2 | 12/2005 |
| WO | WO-2006104143 A1 | 10/2006 |
| WO | 2007002713 A2 | 1/2007 |
| WO | 2007005799 A1 | 1/2007 |
| WO | 2007022395 A1 | 2/2007 |
| WO | 2007029242 A1 | 3/2007 |
| WO | WO-2007044929 A1 | 4/2007 |
| WO | WO-2007083470 A1 | 7/2007 |
| WO | WO-2008034793 A1 | 3/2008 |

OTHER PUBLICATIONS

Nov. 30, 2007 Written Opinion of the International Searching Authority in international application No. PCT/EP2007/058205 filed on Aug. 7, 2007.
Aug. 4, 2008 International Preliminary Report on Patentability in international application No. PCT/EP2007/058205 filed on Aug. 7, 2007.
Nov. 4, 2008 International Search Report in international application No. PCT/EP2008/059040 filed on Jul. 10, 2008.
Nov. 4, 2008 Written Opinion of the ISA in international application No. PCT/EP2008/059040 filed on Jul. 10, 2008.
Sep. 29, 2009 International Preliminary Report on Patentability in international application No. PCT/EP2008/059040 filed on Jul. 10, 2008.
Jul. 17, 2009 Non-final Office Action in U.S. Appl. No. 10/824,033, filed Apr. 14, 2004.
Dec. 15, 2005 International Search Report in international application No. PCT/US2005/019860 filed on Jun. 6, 2005.
Dec. 15, 2005 Written Opinion of the international searching authority in international application No. PCT/US2005/019860 filed on Jun. 6, 2005.
Dec. 4, 2006 International Preliminary Report on Patentability in international application No. PCT/US2005/019860 filed on Jun. 6, 2005.
Apr. 27, 2007 Written Opinion of the ISA in international application No. PCTUS2007000834 filed on Jan. 12, 2007.
Jul. 15, 2008 International Preliminary Report on Patentability in international application No. PCTUS2007000834 filed on Jan. 12, 2007.
Jan. 19, 2007 International Search Report in international application No. PCT/US2006/032228 filed on Aug. 16, 2006.
Jan. 19, 2007 Written Opinion of the ISA in international application No. PCT/US2006/032228 filed on Aug. 16, 2006.
Feb. 20, 2008 International Preliminary Report on Patentability in international application No. PCT/US2006/032228 filed on Aug. 16, 2006.
Jul. 10, 2002 International Search Report in international application No. PCT/EP2002/04727 filed on Apr. 29, 2002.
Jan. 7, 2003 International Preliminary Examination Report in international application No. PCT/EP2002/04727 filed on Apr. 29, 2002.
Nov. 12, 2008 Non-Final Office Action in U.S. Appl. No. 11/652,737, filed Jan. 12, 2007.
May 27, 2009 Final Office Action in U.S. Appl. No. 11/652,737, filed Jan. 12, 2007.
Oct. 27, 2009 Non-Final Office Action in U.S. Appl. No. 11/652,737, filed Jan. 12, 2007.
Apr. 4, 2008 Non-Final Office Action in U.S. Appl. No. 10/476,351, filed May 7, 2004.
Oct. 21, 2008 Final Office Action in U.S. Appl. No. 10/476,351, filed May 7, 2004.
Feb. 4, 2009 Final Office Action in U.S. Appl. No. 10/476,351, filed May 7, 2004.
Jan. 21, 2004 International Search Report in international application No. PCT/EP2002/06784 filed on Jun. 19, 2002.
Apr. 14, 2004 International Preliminary Examination Report in international application No. PCT/EP2002/06784 filed on Jun. 19, 2002.
Apr. 27, 2007 International Search Report in international application No. PCT/US2007/000834 filed on Jan. 12, 2007.
"Medtronic Announces FDA Clearance of Bridge SE Biliary Stent." Business Wire, Oct 15, 2001. wvvw.medtronic.com/newsroom/news_20011015a.html.
"Summary for the Bridge SE Biliary Self-Expanding Stent Delivery System" Jan. 14, 2002 FDA Section 510 (k) review.
Bridge SE Binary System, Oct. 2002, 3 pages, http:/www.medtronicave/com/includes/content/phsycians/bridges/htm.
EP 10001359.8 filed Aug. 16, 2006 European Search Report dated May 28, 2010.
U.S. Appl. No. 10/476,351, filed May 7, 2004 Notice of Allowance dated Mar. 12, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26, 2009.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated Jun. 10, 2010.

* cited by examiner

VARIABLE SPEED STENT DELIVERY SYSTEM

CROSS REFERENCE TO A RELATED PATENT APPLICATION

Priority is herewith claimed under 35 U.S.C. §119(e) from co-pending Provisional Patent Application No.: 60/709,314, filed Aug. 17, 2005, entitled "VARIABLE SPEED STENT DELIVERY SYSTEM". The disclosure of this Provisional Patent Application is incorporated by reference herein in its entirety.

FIELD OF THE INVENTION

The present invention relates, in general, to medical devices, e.g., expandable stents, and, more particularly, to an enhanced method of delivering medical devices into a body lumen, such as a blood vessel, at a delivery rate or speed that varies from a relatively slow initial delivery speed during initial positioning to increasingly faster delivery speed along the remaining length of the stent.

BACKGROUND OF THE INVENTION

Atherosclerosis is the deposition of fatty plaques on the luminal surface of arteries, which in turn causes narrowing of the cross-sectional area of the artery. Ultimately, this deposition blocks blood flow distal to the lesion causing ischemic damage to the tissues supplied by the artery. Atherosclerosis of the arteries, coronary or peripheral, is a pervasive disease. For example, coronary artery atherosclerosis disease (CAD) is the most common, serious, chronic, life-threatening illness in the United States, affecting more than 11 million persons. The social and economic costs of atherosclerosis vastly exceed that of most other diseases. Narrowing of the coronary artery lumen causes destruction of heart muscle resulting first in angina, followed by myocardial infarction and finally death. There are over 1.5 million myocardial infarctions in the United States each year, and six hundred thousand (or 40%) of those patients suffer an acute myocardial infarction and more than three hundred thousand of those patients die before reaching the hospital (Harrison's Principles of Internal Medicine, 14th Edition, 1998). Narrowing of the peripheral arteries is debilitating and can severely affect the quality of life of afflicted patients.

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expansible distal end usually in the form of an inflatable balloon is inserted into a peripheral artery and threaded through the arterial system into the blocked artery and is positioned in the blood vessel at the stenotic site. The balloon is then inflated to flatten the obstructing fatty plaque and dilate the vessel, thereby restoring adequate blood flow beyond the diseased region. Other procedures for opening stenotic regions include directional arthrectomy, rotational arthrectomy, laser angioplasty, stenting, and the like. While these procedures have gained wide acceptance (either alone or in combination, such as PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. Acutely, restenosis involves recoil and shrinkage of the vessel, which are followed by proliferation of medial smooth muscle cells. This proliferation of smooth muscle cells re-narrows the lumen that was opened by the angioplasty within a few weeks to a few months, thereby necessitating a repeat PTA or other procedure to alleviate the restenosis. As many as 50% of the patients who are treated by PTA require a repeat procedure within six months to correct restenosis.

Narrowing of the arteries can occur in vessels other than the coronary arteries, including, but not limited to, the aortoiliac, infrainguinal, distal profunda femoris, distal popliteal, tibial, subclavian, mesenteric, carotid, and renal arteries. Peripheral artery atherosclerosis disease ("PAD", also known as peripheral arterial occlusive disease) commonly occurs in arteries in the extremities (feet, hands, legs, and arms). Rates of PAD appear to vary with age, with an increasing incidence of PAD in older individuals. Data from the National Hospital Discharge Survey estimate that every year, 55,000 men and 44,000 women have a first-listed diagnosis of chronic PAD and 60,000 men and 50,000 women have a first-listed diagnosis of acute PAD. Ninety-one percent of the acute PAD cases involved the lower extremity. The prevalence of comorbid CAD in patients with PAD can exceed 50%. In addition, there is an increased prevalence of cerebrovascular disease among patients with PAD.

A number of different techniques have been used to overcome the problem of restenosis, including treatment of patients with various pharmacological agents or mechanically holding the artery open with a stent or synthetic vascular graft (Harrison's Principles of Internal Medicine, 14th Edition, 1998). Of the various procedures used to overcome restenosis, stents have proven to be the most effective. Stents are metal scaffolds that are permanently implanted in the diseased vessel segment to hold the lumen open and improve blood flow. Placement of a stent in the affected arterial segment thus prevents recoil and subsequent closing of the artery.

There are broadly two types of stents: self-expanding stents and balloon expandable stents. Stents are typically formed from malleable metals, such as 300 series stainless steel, or from resilient metals, such as super-elastic and shape memory alloys, e.g., Nitinol™ alloys, spring stainless steels, and the like. They can also, however, be formed from non-metal materials such as non-degradable or biodegradable polymers or from bioresorbable materials such as levorotatory polylactic acid (L-PLA), polyglycolic acid (PGA) or other materials such as those described in U.S. Pat. No. 6,660,827.

A variety of stent geometries are known in the art, including, without limitation, slotted tube type stents, coiled wire stents and helical stents. Stents are also classified into two general categories based on their mode of deployment. The first type of stent is expandable upon application of a controlled force, such as the inflation of the balloon portion of a dilatation catheter that upon inflation of the balloon or other expansion methods expands the compressed stent to a larger, fixed diameter to be left in place within the artery at the target site. The second type of stent is a self-expanding stent formed from shape memory metal or super-elastic alloy such as nickel-titanium (NiTi) alloys that automatically expands or springs from a compressed state to an expanded shape that it remembers.

Exemplary stents are described in U.S. Pat. No. 4,553,545 to Maass et al.; U.S. Pat. Nos. 4,733,665 and 4,739,762 to Palmaz; U.S. Pat. Nos. 4,800,882 and 5,282,824 to Gianturco; U.S. Pat. Nos. 4,856,516, 4,913,141, 5,116,365 and 5,135,536 to Hillstead; U.S. Pat. Nos. 4,649,922, 4,886,062, 4,969,458 and 5,133,732 to Wiktor; U.S. Pat. No. 5,019,090 to Pinchuk; U.S. Pat. No. 5,102,417 to Palmaz and Schatz; U.S. Pat. No. 5,104,404 to Wolff; U.S. Pat. No. 5,161,547 to Tower; U.S. Pat. No. 5,383,892 to Cardon et al.; U.S. Pat. No. 5,449,373, 5,733,303, 5,843,120, 5,972,018, 6,443,982, and 6,461,381 to Israel et al.; U.S. Pat. Nos. 5,292,331, 5,674,278, 5,879,382 and 6,344,053 to Boneau et al.; U.S. Pat. Nos. 5,421,955, 5,514,154, 5,603,721, 5,728,158, and 5,735,893 to Lau; U.S. Pat. No. 5,810,872 to Kanesaka et al.; U.S. Pat. No. 5,925,061 to Ogi et al.; U.S. Pat. No. 5,800,456 to Maeda et al.; U.S. Pat. No. 6,117,165 to Becker; U.S. Pat. No. 6,358,274 to Thompson; U.S. Pat. No. 6,395,020 to Ley et al.; U.S. Pat. Nos. 6,042,597 and 6,488,703 to Kveen et al.; and U.S. Pat. No. 6,821,292 to Pazienza et al., which are all incorporated by reference herein.

Stents are usually delivered in a compressed condition to the target site and then, deployed at that location into an expanded condition to support the vessel and help maintain it in an open position. The delivery system used to implant or deploy at the stent target site in the diseased vessel using a delivery system that comprises a catheter that carries the stent and a control system that allows the stent to be deployed from the catheter into the vessel.

A common method for using such a system to deliver a stent is to advance the catheter into the body of a patient, by directing the catheter distal end percutaneously through an incision and along a body passage until the stent is located within the desired site. The term "desired site" refers to the location in the patient's body currently selected for treatment by a health care professional. After the stent is deployed at the desired site, it will tend to resiliently expand to press outward on the body passage.

Like many catheter systems, a stent delivery system is often used with a flexible guidewire. The guidewire is often metal, and is slidably inserted along the desired body passage. The catheter system is then advanced over the guidewire by "back-loading" or inserting the proximal end of the guidewire into a distal guidewire port leading to a guidewire lumen defined by the catheter system.

Many catheter systems define guidewire lumens that extend along the entire length or almost all of the catheter. These catheter systems are described as "over-the-wire" catheters, in that the guidewires resides inside a catheter lumen throughout the length of the catheter. Over-the-wire catheter systems provide several advantages, including improved trackability, preventing prolapse of the guidewire, the ability to flush the guidewire lumen while the catheter is in the patient, and the capability of easily removing and exchanging the guidewire while retaining the catheter in a desired position in the patient.

In some circumstances it may be desirable to provide a "rapid-exchange" catheter system, which offers the ability to easily remove and exchange the catheter while retaining the guidewire in a desired position within the patient. Rapid exchange catheters are disclosed in U.S. Pat. Nos. 5,380,283 and 5,334,147 to Johnson; U.S. Pat. No. 5,531,690 to Solar; U.S. Pat. No. 5,690,644 to Yurek et al.; U.S. Pat. No. 6,613,075 to Healy et al.; and U.S. Re. Pat. No. 36,104 to Solar.

Rapid-exchange dilatation catheters are capable of advancement into the vascular system of a patient along a pre-positioned guidewire, for balloon angioplasty or a similar procedure. The guidewire occupies a catheter lumen extending only through a distal portion of the catheter. With respect to the remaining proximal catheter portion, the guidewire exits the internal catheter lumen through a proximal guidewire port, and extends in parallel along the outside of the catheter proximal portion. Of course, the entire catheter and guidewire assembly is typically contained within the lumen of a guiding catheter, which retains a majority of the catheter and guidewire effective lengths together.

Because a majority of the guidewire is outside the catheter shaft, it may be manually held in place as the catheter is removed. Moreover, because the distal catheter guidewire lumen is shorter than the guidewire length that remains outside the patient, the catheter may be removed while also holding the guidewire, until the guidewire may be grasped at a point distal of the catheter. Completing a catheter exchange simply requires reversing the removal process. This rapid exchange technique enables a single physician to exchange balloon catheters, without requiring guidewire extension to temporarily double the guidewire length.

Stent delivery systems must ideally possess certain characteristics. For example, the stent delivery system should preferably protect the stent from damage or deformation during delivery. It is further desirable that the stent delivery system be flexible and able to push through and traverse as many different anatomical arrangements and stenosis configurations as possible. In addition, the stent delivery system should provide for high visibility under fluoroscopy. Often the stent delivery system will be used in conjunction with an outer guiding catheter, which surrounds and guides the stent delivery system to the desired site. The visibility of the stent delivery system on a fluoroscope may be affected by the size of the lumen through which radiopaque contrast fluid is injected. This fluid is generally injected through the annular space between the guiding catheter and the stent delivery system. The visibility can, therefore, preferably be increased by further reducing the outer diameter of the stent delivery system.

Moreover, the stent delivery system should preferably have a positive mechanism for retaining the stent on the catheter prior to deployment and then releasing and deploying the stent at the desired site. Thus, a delivery system for implanting a self-expanding stent may include an inner catheter or tube upon which the compressed or collapsed stent is mounted and an outer restraining sleeve or sheath that is initially placed over the compressed stent prior to deployment. When the stent is to be deployed in the body vessel or accurately positioned at a damaged site, the outer sheath is moved in relation to the inner tube to "uncover" the compressed stent, allowing the stent to assume its expanded condition. Some delivery systems utilize a "push-pull" type technique in which the outer sheath is retracted while attempting to retain the inner lumen stationary. The delivery system may also use an actuating wire that is attached to the outer sheath. When the actuating wire is pulled to retract the outer sheath and deploy the stent, the inner lumen remains stationary, preventing the stent from moving axially within the body vessel. Many different type of delivery systems have been developed for delivering self-expanding stents, but most require a retractable outer sleeve or sheath.

Because of the narrowness of the human vasculature self-expanding stents, generally, are retained in a highly compressed state within the sheath. As a result of the compressive forces necessary to compress the stent to a small diameter within the sheath or sleeve relatively large forces are required to retract the sheath from the stent. Currently, stent delivery systems utilize hand held devices with pivoting levers to provide the necessary forces to retract the sheath from the stent, i.e., deploy the stent.

In addition to overcoming the sheath retraction problem, a delivery system for self-expanding stents must desirably provide variable speed delivery. Preferably, the delivery system should allow the self-expanding stent to be deployed slowly at first to allow the stent to be accurately positioned at a target site within the vasculature. Once positioned and impinged against the inner vessel wall, it is desirable to provide for more rapid deployment to maintain the position and to increase the speed of the overall procedure. As more of the stent impinges against the wall of the body lumen, the speed of deployment can continue to increase because there is more stent contacting the wall and resisting movement of the stent from its originally deployed position and, therefore, less risk of the stent movement. Hence, there is a need for a delivery system that provides a delivery or deployment speed for self-expanding stents that continues to increase along the length of the stent from a relatively low initial deployment speed to a relatively fast deployment speed as the final portion of the stent is released from the sleeve or sheath.

Some attempts have been made to produce devices that can be operated with a single hand so as to allow a physician to use the free hand to control the movement of the delivery catheter. While generally allowing the user to maintain hand position, these devices have typically not provided a variable rate of deployment of the stent. Two-handed devices have been developed to provide some variable speed capabilities, but these devices generally require the user to alter their hand positions to obtain the variable or differing speeds, which is not desirable as it can lead to inaccurate placement of the stent. These multi-speed devices have used a screw-type mechanism to retract the sheath slowly and then, a sliding mechanism to retract the sheath more quickly. Switching between the two retraction mechanisms requires the user to change hand positions during the deployment of the stent.

Hence, there remains a need for an improved variable speed stent delivery system. Preferably, such a system would allow a user to vary the speed of stent deployment or sheath retraction without requiring a change of hand positions. Additionally, such a delivery system preferably is configured to overcome friction between the sheath and compressed stent in a relatively smooth or fluid manner to facilitate accurate positioning of the stent within a body lumen.

SUMMARY OF THE INVENTION

The present invention addresses the above problems by providing a delivery system for deploying stents at a deployment speed that ranges from an initial, relatively slow speed to a final, relatively fast speed. Generally, the delivery system includes a catheter assembly including a guide tube, a retractable sheath slidably mounted on the guide tube, and when loaded, a stent in a compressed state sandwiched between the guide tube and the retractable sheath. A hand-operated deployment assembly is provided in the delivery system that includes a handle housing and one or more rotary knobs or other devices to allow a user to apply a motive force or rotation rate. Within the housing, the retractable sheath is attached to a slider block that is mounted in the handle housing for linear motion, such as by mounting on a slide rod. The slider block is also attached to a flexible drive member, such as a belt segment. A take up pulley is provided in the housing that is connected to the rotary knob, such as by an axle keyed to the pulley and to the knob, to turn at the user input rate. The drive member is attached to the take up pulley such that when the pulley rotates the drive member is wound onto the pulley. The pulley may have a conical cross section to provide a variable speed or as in one embodiment of the invention, a variable overall outer diameter is provided by causing the drive member to be wound upon itself or previously wound portions or thickness. As a result, the retraction or deployment speed automatically increases along the length of the stent being deployed as the overall diameter of the take up pulley increases as a user turns the knob. Hence, for a relatively constant input rotation speed, a substantially continuously increasing deployment speed is produced by the delivery system of the invention.

More particularly, a stent delivery system is provided for deploying a stent at variable speeds. The stent delivery system comprises a catheter assembly having an elongate guide member and an elongate sheath including a lumen in which the guide member is positioned. The sheath is movable relative to the guide member from an initial position in which a loaded stent is sandwiched between the sheath and the guide member to a final position in which the stent is exposed or not restrained by the sheath. The delivery system further includes a deployment assembly having a connector element attached on one side to the sheath. The deployment assembly includes a variable speed mechanism attached to the connector element and operable to move the connector element from a first position to a second position at a retraction speed that varies from an initial speed to a higher final speed. By moving the connector element, the attached sheath is moved from the initial position to the final position at the retraction speed.

According to one aspect of the invention, the retraction speed increases from the first position to the second position of the connector element substantially continuously. The connector element is typically moved along a linear path and the retraction speed can be measured as an increasing linear velocity of the connector element and attached sheath. The variable speed mechanism in one embodiment includes a slide rod mating with an opening or passageway in the connector element so that the connector element is able to slide along the length of the slide rod from its first to its second position. The mechanism further includes a take up pulley and a drive belt or belt segment attached at a first end to the connector element and at a second end to the take up pulley. A knob or other user input device is provided in the deployment assembly for allowing a user to apply a motive force or input rotation rate. The knob is connected to the take up pulley to rotate the pulley at the input rotation rate. When the pulley rotates, the drive belt is wound onto a contact surface of the take up pulley to move the connector element. The retraction speeds are varied or increased with the rotation of the pulley with the drive belt being wound not just on the pulley but also upon previously wound portions or thicknesses of the drive belt. As the overall diameter of the take up pulley increases, the linear velocity of the drive member, i.e., the retraction speed of the connector element and sheath and deployment speed of the stent, also increases for a single input rotation rate. As a result, the delivery system provides a relatively slow initial stent deployment speed to position the stent and, then, continuously increasing deployment speed to rapidly deploy the remaining portions of the stent.

BRIEF DESCRIPTION OF THE DRAWINGS

FIG. 1 is an exploded perspective view of a hand-operated deployment assembly according to one embodiment of the invention illustrating the use of a drive belt (or belt segment)

in combination with a take up pulley to which one end of the drive belt is rigidly attached to provide continuously variable deployment speed;

DETAILED DESCRIPTION OF THE PREFERRED EMBODIMENTS

The present invention is directed to a device, and associated method, for delivering stents at a continuously variable speed. More particularly, the variable speed stent delivery system of the present invention is configured for delivering self-expanding stents at speeds that continuously increase from a relatively slow initial deployment speed to a significantly faster final deployment speed. The continuously variable speeds or continuously increasing speeds with the deployed length of the stent facilitates accurate positioning and initial impingement of the deployed portions of the stent against the inner wall of a body lumen while also improving the efficiency of the procedure by reducing the time to deploy the later portions of the stent and reducing risks of the stent being dislodged as the stent is rapidly deployed once positioned.

In general, delivery systems for self-expanding stents include a catheter assembly and a handle or control handle. A proximal end of the catheter assembly is coupled to the handle, and the catheter assembly extends outwardly from the handle. While the catheter assembly may be any useful length, the assembly in one embodiment is preferably between about 50 cm and 200 cm in length.

The catheter assembly comprises coaxial inner and outer tubes. The outer tube is a tubular sheath and the inner tube is a guide tube (or shaft). The sheath has a lumen extending from a proximal end to a distal end, and a stent, such as a self-expanding stent is mounted on the guide tube, and positioned or housed in a compressed state within a distal area of the lumen of the sheath. As will be explained in detail with reference to FIG. 1-4B, the sheath is attached to the handle such that it can be retracted into the handle to expose or release the compressed stent during deployment. The guide tube is secured to the handle.

The shaft has proximal and distal ends, wherein the proximal end of the shaft has a Luer guidewire hub attached thereto. The proximal portion of the shaft is preferably made from a relatively stiff material such as stainless steel, Nitinol, or any other suitable material known to those of ordinary skill in the art. The shaft also includes a distal portion, which is preferably made from a co-extrusion high density polyethylene for the inner portion and polyamide for the outer portion. Other suitable materials for distal portion known to those of ordinary skill in the art include polyurethane, polyimide, polyetheretherketone, and Nitinol. These materials may be utilized as single or multi-layer structures, and may also include reinforcement wires, braid wires, coils, filaments or the like. The two portions, distal and proximal, of the shaft are joined together by any number of means known to those of ordinary skill in the art including heat fusing, adhesive bonding, chemical bonding or mechanical attachment. The stainless steel proximal end gives the shaft the necessary rigidity or stiffness it needs to effectively push out the stent, while the distal portion provides the necessary combination of flexibility, to navigate tortuous vessels, and column strength to effectively push out the stent.

Preferably, the distal portion of the shaft has a distal tip attached thereto. The distal tip can be made from any number of materials known in the art including polyamide, polyurethane, polytetrafluoroethylene, and polyethylene including multi-layer or single layer structures. The distal tip has a proximal end whose diameter is substantially the same as the outer diameter of the sheath which is immediately adjacent thereto. The distal tip tapers to a smaller diameter from its proximal end to its distal end, wherein the distal end of the distal tip has a diameter smaller than the inner diameter of the sheath. The distal tip helps to prevent blood from entering the sheath as the apparatus is being navigated through the body vessels. In a preferred embodiment, attached to distal portion of the shaft is a stop, which is proximal to the distal tip and the stent. The stop can be made from any number of materials known in the art, including stainless steel, and is even more preferably made from a highly radio-opaque material such as platinum, gold, tantalum, or radio-opaque filled polymer. The stop can be attached to the shaft by mechanical or adhesive bonding, or by any other means known to those skilled in the art. Preferably, the diameter of the stop is large enough to make sufficient contact with the loaded stent at its end without making frictional contact with the inner layer of the outer sheath. The stop helps to "push" the stent out of the sheath during deployment, by preventing the stent from migrating proximally within the sheath during retraction of the sheath for stent deployment.

In one embodiment, proximal to the stop is a sleeve, which can be made from any number of materials known to those skilled in the art including plastic. The sleeve is attached to the shaft immediately proximal to the stop by any number of ways known to those skilled in the art including thermal or mechanical bonding. The sleeve acts to reinforce the stop during deployment of the stent. The sleeve is large enough to make sufficient contact with the stop in order to reinforce the stop. However, it is also preferably small enough not to interfere with the taper of outer sheath when the inner shaft is inside the outer sheath. During deployment, the outer sheath is moved in a proximal direction relative to the stationary inner shaft. The radio-opaque stop also aides in positioning the stent within the target lesion during deployment within a vessel, as is described below.

A radio-opaque marker is attached to the shaft at a point distal to the distal end of the loaded stent. The marker can be made of platinum, iridium coated platinum, gold, tantalum, stainless steel or any other suitable material known in the art. Preferably, the shaft has a guidewire lumen extending along its length, where the guidewire enters through the guidewire hub and exits through its distal tip. This allows the shaft to receive a guidewire much in the same way that a balloon angioplasty catheter receives a guidewire. Such guidewires are well known in the art and help to guide catheters and other medical devices through the vasculature of the body.

Alternatively, the shaft of the present invention may comprise three tubing sections (proximal shaft, distal shaft, and distal tip). The proximal shaft may be constructed of 304 stainless steel hypo-tubing (O.D.=0.032" and wall thickness=0.0045") and be approximately 10-12 inches long. The proximal end of the proximal shaft is attached to a typical medical luer connector or "hub". Use of the stainless hypo-tubing will provide the necessary stiffness and column strength to support the system while the outer sheath is retracted for stent deployment. The distal shaft may be constructed of a coextruded tube consisting of an outer layer of nylon-12 (or another suitable polymer) and an inner layer of a maleated high-density polyethylene such as PLEXAR PX209, sold by the Quantum Chemical Company. PLEXAR PX209 is a maleated high-density polyethylene that chemically bonds to nylon-12 in the extrusion process. The distal shaft is designed to take advantage of the properties of nylon-12 while providing a lubricous inner lumen for tracking over a guidewire. Also, PLEXAR PX209 polymer bonds tenaciously to stainless steel in a typical heat fusing process. U.S. Pat. No. 5,538,510, issued on Jul. 23, 1996, which is hereby incorporated herein by reference, discloses the use of such materials in manufacturing catheters. The distal tip of the inner member may be sealed or insert molded to the distal shaft and constructed of an approximate 25D Shore hardness polyamide elastomer or equivalent. Use of nylon-12 as the outer layer of the distal shaft helps to facilitate this seal. The tip is designed to be a traumatic which can be beneficial when working in the carotid region. Being soft and relatively sticky, the tip may be coated with a hydrophilic coating to provide better lubricity.

The sheath is preferably a polymeric catheter and has a proximal end terminating at a Luer hub and a distal end, which terminates at the proximal end of the distal tip of the shaft, when the stent is in un-deployed position. Preferably, the distal end of the sheath includes a radio-opaque marker band disposed along its outer surface. As will be explained below, the stent is fully deployed when the marker band is proximal to the radio-opaque stop, thus indicating to the physician that it is now safe to remove the apparatus from the body.

In one embodiment, the distal end of the sheath includes an enlarged section, which has larger inside and outside diameters than the inside and outside diameters of the sheath proximal to the enlarged section. The enlarged section houses the pre-loaded stent, the stop, the sleeve, and the stent bed, which is the portion of the shaft over which the stent is disposed. Proximal to the sleeve, the outer sheath tapers proximally to a smaller size diameter. The tapering of the sheath allows for higher injection rates of radiopaque fluid, both before and after deployment of the stent.

Often self-expanding delivery systems had problems with the stent becoming embedded within the sheath or catheter in which it is disposed. To overcome this problem, the sheath preferably comprises an outer polymer, preferably polyamide, layer and an inner polymer, preferably polytetrafluoroethylene, layer. Other suitable polymers for the inner and outer layers and include any suitable material known to those skilled in the art including polyethylene, or polyamide, respectively. Positioned between the outer and inner layers is a wire reinforcing layer, which is preferably a braided wire. The braided reinforcing layer is preferably made from stainless steel. The use of braiding reinforcing layers can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

The outer sheath can incorporate a single outer polyamide layer from its proximal end to its distal end or can be a series of fused transitions decreasing in material durometer from the proximal end to the distal end along the outer layer of the sheath. The inclusion of transitions of varying material durometers can effectively enhance the catheter performance as it is pushed over the guidewire through the vascular anatomy. The flexibility of the delivery system from the proximal end to the distal end of the sheath can improve the manner in which the system tracks over the guidewire.

The three layers of the sheath collectively enhance stent deployment. They help to prevent the stent from becoming too imbedded into sheath, prior to stent deployment. The braid layer provides radial support to the inner layer creating sufficient resistance to the outward radial force of the stent within the sheath. The inner layer also provides a low coefficient of friction surface to reduce the forces required to deploy the stent. In addition to the above mentioned benefit, the braid layer offers many other advantages. It gives the sheath better pushability, the ability to transmit a force applied by the physician at a proximal location on sheath to the distal tip, which aids in navigation across tight stenotic lesions within the vascular anatomy. The braid layer also gives the sheath better resistance to elongation and necking as a result of tensile loading during sheath retraction for stent deployment. The configuration of the braid layer can be changed to change system performance. This is achieved by changing the pitch of the braid, the shape of the individual braid wires, the number of braid wires, and the braid wire diameter. Additionally, coils could be incorporated similarly to the braid layer of the sheath to minimize stent embedment and enhance system flexibility. Use of coils in catheters can be found in U.S. Pat. No. 5,279,596 issued to Castaneda et al. on Jan. 18, 1994, which is hereby incorporated herein by reference.

Alternatively, the outer sheath of the system may comprise three tubing sections (proximal sheath, distal sheath, and distal end). The proximal sheath may be constructed of 304 stainless steel hypo-tubing (O.D.=0.065", I.D. 0.053") and be approximately 20 inches long. The proximal end of the proximal shaft is attached to a valve that provides a seal to blood flow when closed, and allows free movement over the inner member when opened. Again, the use of stainless steel for the proximal end will give the physician the necessary stiffness and column strength to manipulate the system for deployment. The distal sheath of the outer member is also constructed of a coextruded tube of nylon-12 over the PLEXAR PX209 polymer. The same logic used above applies. We need lubricity over the inner member (provided by the PLEXAR PX209 polymer) and the push and tracking ability of nylon-12. The distal shaft is again heat fused to the stainless steel hypotube.

When being inserted into a patient, the sheath and the shaft are locked together at their proximal ends by a Tuohy Borst valve. This prevents any sliding movement between the shaft and sheath which could result in a premature deployment or partial deployment of the stent. When the stent reaches its target site and is ready for deployment, the Tuohy Borst valve is opened so that the sheath and the shaft are no longer locked together.

During use, the distal portion of the catheter assembly is positioned within a body lumen or vessel with the stent at a target site. The outer sheath is then retracted so as to deploy the self-expanding stent. In this regard, the stent delivery system further includes a control handle connected to a proximal portion of the catheter assembly and, more particularly to the outer sheath to provide the force to retract the sheath. The handle includes a mechanism for retracting the sheath that comprises a belt (or belt segment) or similar element linked or connected to the outer sheath at first end and to a take up pulley at a second end. The connection to the take up pulley enables the continuously increasing deployment speed (or sheath retraction speed) because when the pulley turns, the belt is taken up onto the pulley causing the overall effective outer diameter of the take up pulley to increase by the thickness of the belt wrapped on the pulley. The belt may have a uniform thickness or variable thickness to provide a desired speed/force profile for the delivery system. The change in deployment speed occurs during each rotation of the pulley with more belt and connected sheath being retracted for each rotation of the pulley, thereby effectively changing the deployment/retraction speed and sheath retraction force output for the same input by the user. The input by the user is typically provided by turning a knob connected, such as by one or more gears, to the take up pulley. In some cases, the take up pulley is a conical pulley to provide the varying speed rather than (or in addition to) relying only on the additive belt thickness to increase the pulley's overall outer diameter.

During deployment the outer sheath is moved toward the handle from an initial position (e.g., a pre-deployment or stent loaded position) toward a fully deployed position. The movement or retraction of the sheath occurs at an initial deployment or retraction speed, $V_1$, in response to a force applied to the proximal end of the outer sheath attached to the handle. The initial velocity, $V_1$, is a relatively low speed to allow the stent to be slowly exposed and to initially expand and impinge on the inner wall of the body lumen at a targeted site. Once initial deployment and/or stent impingement have occurred, the sheath preferably is retracted at higher and higher speeds.

Once the sheath has been retracted fully from the stent the stent expands and impinges against the adjacent inner wall of a body lumen (not shown). The sheath is being retracted at its maximum deployment speed, $V_N$, at a point when the stent is fully deployed. In some embodiments, the sheath is retracted at continually increasing speeds from an initial position, Pos. X, to a final deployment position, Pos. Y. Generally, the retraction length as measured from Pos. X to Pos. Y is at least as long as the length of the stent being deployed but more typically, is slightly longer than the length of the stent to ensure that the stent is allowed to fully deploy and does not bind on the distal end of the sheath. The fully deployed position, Pos. Y, of the sheath relative to the inner catheter shaft may be provided by a stop or other device within the control handle to limit the maximum amount of travel of the sheath and to allow an operator to verify when the stent is deployed and the catheter assembly may be removed from the body lumen.

Prior to describing the control handle in detail, it may be useful again to stress that a number of catheter assemblies (or at least distal portion configurations) and/or stents may be used to practice the invention. In other words, the handle is useful with nearly any catheter assembly that employs a retractable outer sheath with an expandable stent. For example, but not as a limitation, the distal portions or catheter assemblies and/or stents described in the following patents, which are incorporated herein by reference, may be used with handle: U.S. Pat. No. 6,375,676 to Cox; U.S. Pat. No. 6,019,778 to Wilson et al.; U.S. Pat. No. 6,613,075 to Healy et al.; U.S. Pat. No. 6,117,140 to Munsinger; U.S. Pat. No. 6,520,983 to Colgan et al.; U.S. Pat. No. 6,443,979 to Stalker et al.; and U.S. Pat. No. 6,129,755 to Mathis et al.

Figure 1:
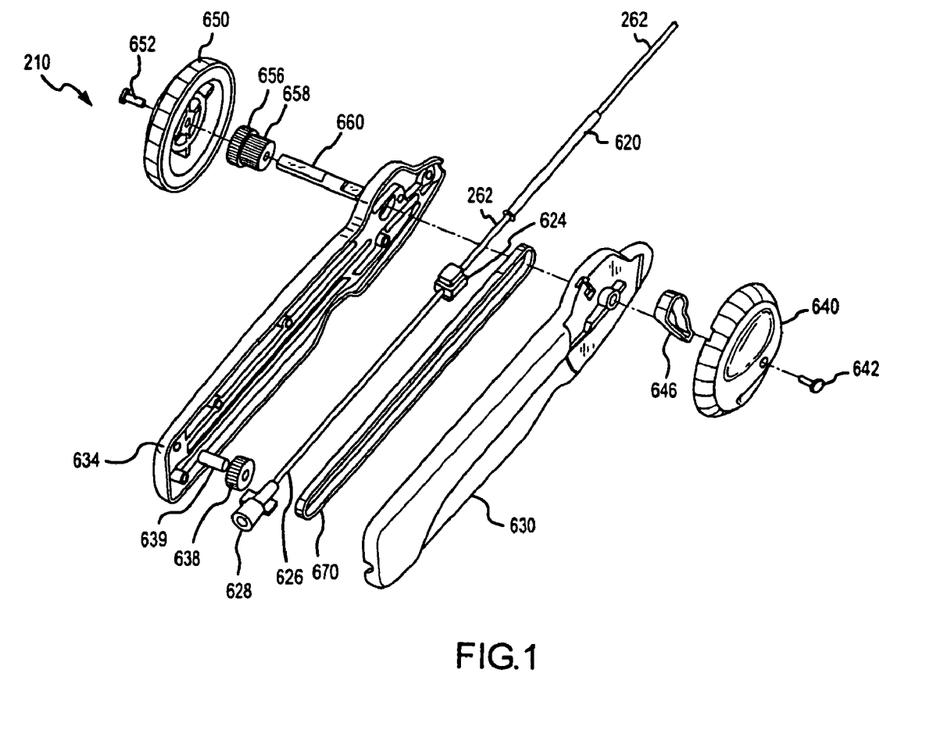

Turning to FIG. 1, an exploded perspective view of one embodiment of the control handle is provided that is adapted to deploy a self-expanding stent at variable speeds or more accurately, at increasing speeds. In this regard, the outer sheath 262 is rigidly attached to the handle 210 at a slide block 624 with a protective sleeve 620 being optionally provided for additional rigidity in the catheter assembly 252 adjacent the handle 210. The slide block 624 may take a number of forms to provide the function of connecting or bonding to the sheath 262 and of sliding or moving in response to manipulation of the handle by a user or operator.

To provide selective movement, the slide block 624 includes a channel or, more preferably, an enclosed passageway through which a slide rod 626 passes during operation of the handle 210. In other words, the slide block 624 engages one end of slide rod 626 when the outer sheath 262 is in the extended (or non-extracted or initial or stent loaded) position. The slide rod 626 is attached at the other end to a female luer hub 628, which may optionally be used to pass a guide wire through the slide rod 626, outer sheath 262, and inner catheter shaft 310 via lumen 412. The hub 628 is rigidly mounted within the right and left handle housings 630, 634. The housings 630, 634 include tracks or recessed areas for the slide rod 626 and for the slide block 624 to travel along the slide rod 626 during operation of the handle 210.

A belt or belt segment 670 is provided to apply a force on the slide block 624 and, hence, on the outer sheath 262 to retract the sheath 262. As shown more clearly in FIG. 2, the slide block 624 is attached on one side to the outer sheath 262 at a connection point 710 and on the other to a first end of the belt segment 670 at a connection point 720. The hub 628 is shown to be mounted into the housing 634 and is connected rigidly to the slide rod 626. The slide block 624 engages, at least partially, the slide rod 626 such that when the belt 670 is pulled or moved toward the hub 628 the slide block 624 further engages the slide rod 626 and moves toward the hub 628 pulling along the rigidly attached outer sheath 262. The belt segment 670 may take many configurations and be fabricated from numerous materials to practice the invention. In one embodiment, the segment 670 is about 10 inches long, 0.25 inches wide and 0.050 inches thick (tapered) but of course, these dimensions may vary significantly with this just being one example. The segment 670 may be made of rubber, RTV, urethane, metal or the like and may be reinforced such as with fiberglass, nylon, and the like or a metal. Additionally, in some cases, the belt segment 670 may take the form of a cable, chain, or other useful connection member.

Figure 2:
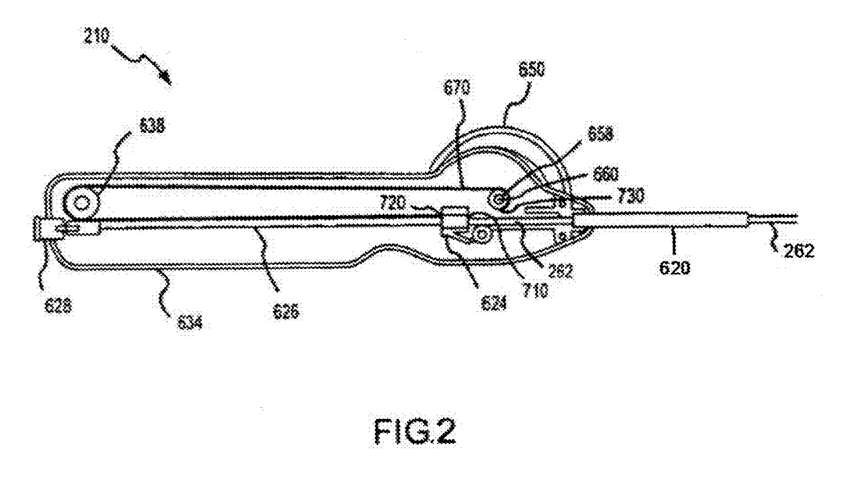
FIG. 2 is a side view of the hand-operated deployment assembly of FIG. 1 with a housing segment removed showing the sheath attached to a slide block and the drive belt being attached to the slide block at one end and the take up pulley at the other end.

With reference to FIGS. 1 and 2, the handle 210 achieves the variable speed through the combination of an idler pulley 638, which may be mounted to the housing with a dowel pin or shaft 639, the belt 670, and pulley 656. The idler pulley 638 is mounted within the housings 630, 634 to be free to rotate, and supports the belt 670. The idler pulley 638 is also used to direct the forces applied to the belt 670 in a direction substantially parallel to the slide rod 626 to more effectively retract and extend the sheath 262 in response to movement of the belt 670. The pulley 638 may have smooth surfaces or as shown, have external teeth to better mate with the inner surface of the belt 670 and minimize slippage. The pulley 638 may also include a track or channel for receiving the belt 670 to control side-to-side movement or the positioning of the belt 670 relative to the pulley 638 may be maintained by the internal housing configuration, e.g., by placing walls or structures in handle housings 630, 634 to prevent excess side-to-side movement of the belt 670 once it is positioned about the circumference of the pulley 638.

The belt 670 is attached at a second end 730 to a take up pulley 656. The belt 670 is attached at 730 to the pulley 656 and wrapped at least partially about the circumference of the take up pulley 656. As a result, the belt 670 is wrapped about the circumference of the take up pulley 656 effectively increasing the outer diameter of the pulley 656 as the belt 670 becomes layered upon itself with each rotation of the pulley 656. As shown, the pulleys 638 and 656 are typically aligned within a single plane so as to more effectively apply or transfer the forces applied to the pulley 656 by an operator to the belt 670 and attached slide block 624 and outer sheath 262.

To allow a user to readily input forces to the belt 670, the handle 210 includes right and left knobs 640, 650, which may be attached with screws 642, 652 or other mechanical means. A shipping lock 646 is optionally provided for locking the knobs 640, 650 during shipment and storage. The knobs 640, 650 may include surfaces or other features to improve gripping by a user, such as rubber or plastic contact surfaces and/or recessed areas for placing fingers within the knobs 640, 650. Further, the knobs 640, 650 may be replaced by other mechanical devices for applying force in a substantially circular pattern such as those found in a reel (i.e., fishing reel) to reduce the need for a user to change hand positions during stent deployment. As will be understood, a person of ordinary skill in the art can use various configurations of the knobs or external force transmission devices 640, 650, all of which are contemplated to be within the scope of the invention.

The take up pulley 656 is housed within the housings 630, 634 as shown in FIG. 2. The pulley 656 may be part of a combination gear 658 and is keyed or rigidly attached to a knob axle 660 which in turn is mounted into or attached to the knobs 640, 650. Hence, when either of the knobs 640, 650 is rotated by a user, the knob axle 660 rotates causing the affixed take up pulley 656 to rotate a similar number of rotations in the same direction. Again, the handle housings 630, 634 are preferably configured to provide space for the pulley 656 to freely rotate with a number of layers of the belt 670 wrapped around its exterior surface, but also with not excessive space to keep the wrapped belt 670 from slipping off of the pulley 656 toward either of the handle housings 630, 634. This space for expansion of the take up pulley 656 outer diameter is shown in FIG. 2.

As discussed, the belt 670 may be formed with a uniform thickness or of varying thickness to obtain a desired deployment speed/force profile. For example, the belt 670 may be thinner proximal to the take up pulley 656 and thicker distal to the take up pulley 656 so as to more gradually increase speed from the initial deployment or retraction speed to the final deployment or retraction speed. As the belt 670 is taken up onto the pulley 656, the diameter of the pulley 656 changes with the thickness profile of the belt 670 wrapped upon the pulley 656. The change in pulley outer diameter changes the amount of sheath 262 that is retracted for each rotation of the take up pulley 656. The control handle 210 of the invention is able to change the speed of sheath retraction and the sheath retraction force output for the same input by the user, i.e., more sheath is retracted for each turn of the knobs 640, 650.

The pulleys 638, 656 may be formed from a number of materials to practice the invention such as plastic (such as Delran, ABS, nylon, acrylic, and the like), metals (such as brass, SS, aluminum, and the like), or other useful material. Further, the number and configuration of the pulleys 638, 656 may vary with those illustrated in FIGS. 1 and 2 providing one useful example. For example, the pulley 656 may be replaced with one or more gears or pulleys. Further, the pulley 656 may be replaced with another device that is useful for taking up the belt segment 670 and increasing in diameter to provide the continuously variable speed of the invention. In one embodiment (not shown), the pulley 656 is replaced with a cam shaped member that has a shape (or increasing cross section) that has a shape selected such that the shape of the cam shaped member itself affects or even defines the stent delivery speed achieved. In another embodiment (not shown), a lead or drive screw having a variable pitch is utilized. Hence, once the concept of a variable speed delivery system is understood from the present description, many additional embodiments will become apparent to those skilled in the art and are considered within the breadth of this description and the attached claims.

Figure 3A:
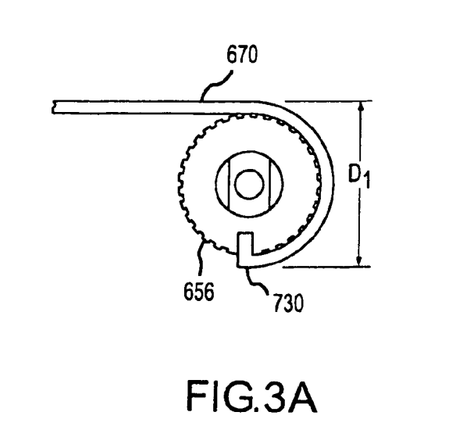
FIGS. 3A and 3B illustrate a side view of a belt and a take up pulley in an initial position and a schematic of the belt and gear in the initial position showing initial dimensions along with linear velocity of the drive belt and angular velocity of the pulley.
Figure 3B:
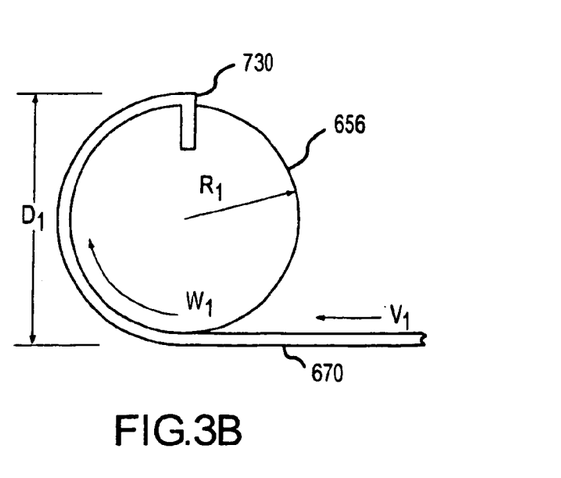

The functioning of the handle 210 and its take up pulley 656 is now more fully explained with reference to FIGS. 3A-4B. In these figures, the following symbols are used:

FIGS. 3A and 3B illustrate the take up pulley 656 in its initial position with the belt Symbols
$\omega_1 = \omega_2$ = Angular Speed = user input
$\tau_1 = \tau_2$ = Torque = user input
$F_1$ = Input Force (user)
$F_{(n+1)}$ = Variable Output Force to Retract Sheath
$R_1$ = Initial Pulley Radius
$R_{(n+1)}$ = Variable Pulley Radius
$V_1$ = Initial Belt Takeup Linear Speed
$V_{(n+1)}$ = Variable Belt Takeup Linear Speed
Recall
$V = \omega R$
$\tau = R \times F$ 670 attached to the pulley 656 at 730. This is the position the belt and pulley would be in when a stent is loaded in the catheter assembly for deployment, e.g., this can be thought of as a pre-deployment position or state of the handle 210. In this position, the outer sheath would be covering the stent preventing it from expanding or deploying. As shown, the initial outer diameter, $D_1$, is measured as including the pulley 656 outer diameter and also at least one thickness of the belt 670 but typically two thicknesses as shown. When the knob is turned, an angular velocity or speed, $\omega_1$, is imparted to the pulley 656 and is translated to a linear velocity of the belt 670 or deployment speed, $V_1$, based upon the initial radius, $R_1$, of the take up pulley 656 including any belt thicknesses, i.e., $V = \omega R$. The velocity of the belt, $V_1$, is substantially equivalent to the speed at which the sheath 262 is retracted (see FIG. 4).

Figure 4A:
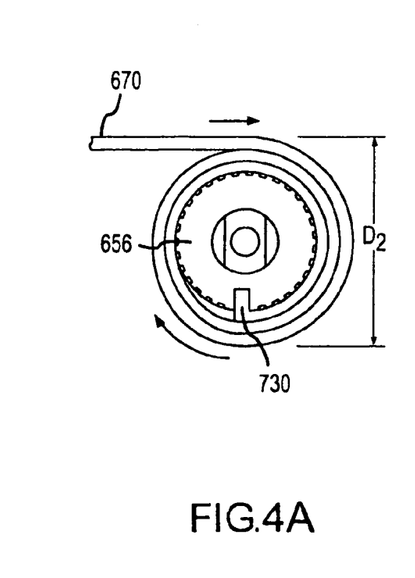
FIGS. 4A and 4B illustrate a side view of the belt and take up pulley of FIG. 3A in a second position in which the radius of the take up pulley radius has increased due the addition of the retracted belt wrapping about the pulley and showing the changed linear velocity of the drive belt and changed angular velocity of the pulley, e.g., increase velocities due to increased outer diameter of the take up pulley.
Figure 4B:
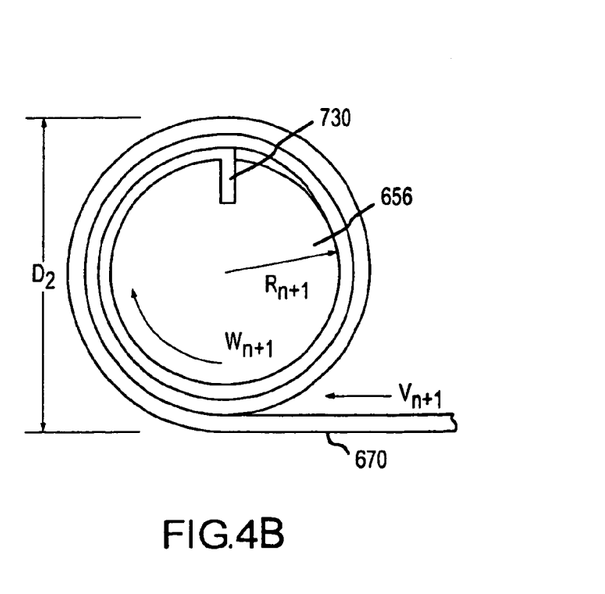

With each rotation of the knobs and linked pulley 656, the deployment speed is increased because the overall outer radius of the pulley 656 is increased by the thickness of the retracted belt. Such a situation is shown in FIGS. 4A and 4B, which show the take up pulley 656 at a second or later time after the pulley 656 has been rotated 1 to 3 times. In this second state, the outer sheath 262 would be retracted at its initial position (e.g., Pos. X in FIG. 5) by the additional length of belt 670 wrapped about the pulley 656 compared with the initial state shown in FIGS. 3A and 3B. As shown, the outer diameter of the take up pulley, $D_2$, has increased by the thickness of the belt 670 that has been retracted since the initial state. This causes the pulley radius, $R_{N+1}$, to likewise increase, which in turn results in the rotation of the knob and affixed pulley 656 to translate into a larger linear velocity, $V_{N+1}$, of the drive belt 670. As a result, the sheath 262 is also retracted quicker and the deployment speed for the stent is substantially increased, e.g., $V_{N+1} = \omega_{N+1} R_{N+1}$ in which $R_{N+1}$ has increased. As will be appreciated, the configuration of the handle 210 results in a retraction or deployment speed that is substantially continuously variable because the speed changes (e.g., increases) with the changing overall outer diameter of the take up pulley 656, which changes nearly continuously with the turning of the connected input knob.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. For example, a conical pulley may be substituted for the take up pulley shown in the figures with the drive belt typically wrapping in a single layer about the circumference of the pulley, with varying speeds being provided by the changing pulley diameter. A conical pulley also facilitates a deployment system in which the speed varies in an opposite manner to that described, i.e., from fast deployment to slow deployment, by attaching the belt to the larger diameter portion of the conical pulley and causing the belt to wrap about the smaller and smaller sections of the take up pulley with each rotation.

Further, it will be understood that the variable delivery speed system of the invention also provides a varying force that is experienced by a user that enhances smooth and accurate placement of stents. More specifically, the friction and other forces resisting deployment are greatest initially and it is desirable to deploy at slower speeds for accurate placement as these forces are overcome. As friction and other resistive forces decrease, the deployment is quickened and the force required to deploy the stent and operate the delivery system decreases, too. Additionally, the stent itself provides spring forces that assist deployment at these later stages of deployment, which further lessens the amount of input force or torque required from the user or operator of the delivery system.

We claim:

1. A delivery system for deploying a medical device at variable speeds, comprising:

a catheter assembly comprising an elongate shaft and an elongate sheath including a lumen in which the shaft is positioned, wherein the sheath is movable relative to the shaft from an initial position in which the medical device is sandwiched between the sheath and the shaft to a final position in which the medical device is exposed; and a control handle comprising a connector element attaching an end of the sheath to the control handle and a variable speed mechanism attached to the connector element, wherein the variable speed mechanism includes:

a rotary knob that is operable at a relatively constant input rotation speed to move the connector element from a first position to a second position at a retraction speed that varies from an initial speed to a final speed that is higher than the initial speed, whereby the attached sheath is moved from the initial position to the final position;

a slide rod mating with a passageway in the connector element, whereby the connector element is able to slide along the length of the slide rod;

a take up pulley;

a drive belt attached at a first end to the connector element and at a second end to the take up pulley, wherein the drive belt is wrapped onto a contact surface of the take up pulley when the take up pulley is rotated and moves the attached connector element at the varying retraction speed; and a translation member rigidly attached to a user input element to rotate with the user input element, wherein the translation member is linked to the take up pulley to rotate at an angular velocity based on the input force, and wherein an overall outer diameter of the take up pulley, comprising an outer diameter of the take up pulley and wrapped portions of the drive belt, increases with rotation of the take up pulley, whereby the angular velocity increases based on the input force with a resultant increase in the retraction speed.

2. The system of claim 1, wherein the retraction speed increases substantially continuously from the initial speed to the final speed.

3. The system of claim 2, wherein the connector element is moved along a linear path and the retraction speed is measured as a linear velocity.

4. The system of claim 1, wherein the variable speed mechanism further comprises an idler pulley mounted within the system to freely rotate and to support the drive belt to pull the connector element toward the idler pulley on the slide rod as the drive belt is wrapped onto the take up pulley.

5. A stent deployment apparatus, comprising:

a shaft having proximal and distal ends;

an expandable stent mounted over the distal end of the shaft;

a retractable sheath slidably mounted on the shaft, the sheath being retractable from a fully extended position in which the stent is covered by the retractable sheath and a fully retracted position in which the stent is exposed;

a take up pulley with a conical contact surface rotating at a fixed user input rotation rate; and a drive belt linked to the retractable sheath and to the take up pulley such that the drive belt wraps onto the contact surface from a smaller cross sectional portion to a larger cross sectional portion.

\* \* \* \* \*